(12) United States Patent
Davidson

(10) Patent No.: US 6,558,629 B1
(45) Date of Patent: May 6, 2003

(54) DEVICE AND METHOD FOR PREPARING TISSUE SPECIMEN FOR HISTOLOGIC SECTIONING

(75) Inventor: Terence Mark Davidson, Poway, CA (US)

(73) Assignee: Bradley Products, Inc., Bloomington, MN (US)

( * ) Notice: Subject to any disclaimer, the term of this patent is extended or adjusted under 35 U.S.C. 154(b) by 0 days.

(21) Appl. No.: 09/711,662

(22) Filed: Nov. 13, 2000

(51) Int. Cl.[7] .................................................. B01L 3/00
(52) U.S. Cl. ........................................ 422/99; 435/40.5
(58) Field of Search ........................... 422/99; 435/40.5; 436/174; 249/139

(56) References Cited

U.S. PATENT DOCUMENTS

| | | | |
|---|---|---|---|
| 2,718,126 A | | 9/1955 | Ball |
| 2,996,762 A | * | 8/1961 | Mcormick ................. 264/238 |
| 3,014,614 A | | 12/1961 | Carroll et al. |
| 3,483,904 A | | 12/1969 | Jacumin |
| RE28,165 E | | 9/1974 | McCormick |
| 3,940,219 A | | 2/1976 | Pickett et al. |
| 3,982,862 A | | 9/1976 | Pickett et al. |
| 4,073,533 A | * | 2/1978 | De bre et al. ............... 294/118 |
| 4,272,049 A | | 6/1981 | Kiindel |
| 4,623,308 A | | 11/1986 | Hellon |
| 4,695,339 A | | 9/1987 | Rada |
| 4,752,347 A | | 6/1988 | Rada |
| 4,760,921 A | * | 8/1988 | Licari ......................... 206/504 |
| 5,044,165 A | | 9/1991 | Linner et al. |
| 5,269,671 A | | 12/1993 | McCormick |
| 5,424,040 A | | 6/1995 | Bjornsson |
| 5,550,033 A | | 8/1996 | Krumdieck |
| 5,628,197 A | | 5/1997 | Rada |
| 5,665,398 A | | 9/1997 | McCormick |

* cited by examiner

Primary Examiner—Jill Warden
Assistant Examiner—Sam P. Siefke
(74) Attorney, Agent, or Firm—Beck & Tysver, P.L.L.C.

(57) ABSTRACT

A receptacle and dipping assembly aid in the preparation of a tissue sample for frozen histologic sectioning. A receptacle receives a tissue sample and O.C.T. compound. A chuck in inserted into the receptacle. A dipping assembly receives the receptacle and holds the chuck in proper orientation while the receptacle is cooled and the O.C.T. and tissue are frozen. The chuck, with the frozen block of O.C.T. and tissue attached thereto, is removed from the receptacle and placed in a microtome for slicing of the tissue.

9 Claims, 13 Drawing Sheets

DEVICE AND METHOD FOR PREPARING TISSUE SPECIMEN FOR HISTOLOGIC SECTIONING

FIELD OF THE INVENTION

The present invention relates generally to a device and method for preparing a tissue specimen for frozen sectioning in surgical pathology, histopathology and MOHS. More particularly, the present invention relates to a device and method for preparing tissue sections for microscopic examination during surgery using frozen section technique for extirpation of neoplasms.

BACKGROUND OF THE INVENTION

Frozen sectioning is used in surgical pathology, histopathology and MOHS to relatively quickly yield tissue sections for microscopic examination. Frozen sectioning is particularly useful for tumor margin analysis. The use of histologic sections guides or assists a surgeon during surgery to determine whether all of the cancerous cells or neoplasm are excised and, if not, where to make further surgical excisions. The technique involves an iterative process of excising tissue, examining it and then excising additional tissue as dictated by the examined tissue sample. More specifically, a portion of tissue is excised and sliced into sections in a microtome. The tissue slices are examined microscopically and then another area is selected for excision based on the examination of the slices. The next tissue sample is excised and the sample is sliced into sections which are examined microscopically to determine whether they contains residual neoplasm. Mapping techniques are used to record tumor location and to determine which tissue adjacent to the previous tissue sample should be excised next. The procedure is repeated until the excised tissue specimen shows no residual neoplasm.

In general, the preparation of tissue slices involves encasing or embedding the tissue specimen in an O.C.T. substance and then slicing the solidified block in a microtome, yielding slices that contain a generally peripheral portion of O.C.T., with an internal portion of tissue section in most of the slices. "O.C.T." stands for "optimal cutting temperature" and, as the name suggests, is a substance that makes it easier to cut or slice the tissue specimen. O.C.T. is typically liquid or semi-liquid at room temperature. It is poured in liquid form over the tissue specimen and then is solidified by cooling it to a temperature below its freezing point.

Typically, an excised tissue portion is generally curved or parabolic in cross-section. However, to obtain tissue slices or sections that are satisfactory for microscopic examination, the face of a specimen to be sectioned should be planar and parallel to the path of relative movement between the microtome knife and the specimen, thus ensuring that all of the surgical margin is included in the first several slices or sections. When performing frozen sections for tumor extirpation, this is of particular importance for accurate histologic or microscopic interpretation. For general diagnostic frozen sectioning, this is advantageous because it saves time. Therefore, the parabolic or curved specimens should be flattened before they are encased in O.C.T. to produce good quality slices. This is often difficult and tedious because the edges of tissue specimens are typically inclined to curl or not lie flat.

The frozen section technique requires the fast preparation and examination of fresh tissue. Therefore, techniques used to prepare fixed tissue for permanent section analysis are not applicable.

One method of preparing fresh tissue samples for slides for use in a frozen section technique is described in U.S. Pat. No. 4,695,339 to Rada. Rada describes placing a tissue specimen on a polished platform, placing a membrane over the specimen, manipulating the specimen with a tool to flatten it on the platform, then using a vacuum device to further flatten the specimen against the platform. Rada then describes freezing the tissue specimen by applying liquid nitrogen to it with a swab. Thereafter, the frozen specimen is entombed in O.C.T. by applying the O.C.T. to the platform that holds the tissue and to another mateable platform. The two platforms are pressed together until the O.C.T. solidifies. The platforms are then pulled apart, and the solidified block of O.C.T with the tissue specimen embedded therein is removed from the platform to which it adheres. This process involves one step for freezing the tissue and then later in the process requires another step for solidifying the O.C.T. Further, the process requires the use of vacuum equipment.

The efficiency and accuracy of the frozen section technique is affected by the quality of the tissue slices. What has been needed is an elegant and effective method and device for preparing tissue slices or sections that allows the entire excised tissue surface to be examined. Further, a method and device are needed which minimize the size, bulk, and power requirements of the equipment involved in the process. Still further, what is needed is a process that reduces the amount of time required for preparing tissue sections.

SUMMARY OF THE INVENTION

The present invention provides a device, method, and kit for preparing tissue samples for sectioning. According to one aspect of the invention, a device is disclosed that includes a cup-shaped receptacle having a planar surface on which a specimen is flattened. The cup shape of the receptacle allows OCT to be poured directly into the cup over the specimen. The receptacle accommodates a chuck member that has a planar surface sized to be received in the cup-shaped receptacle.

According to another aspect of the invention, a method is disclosed for preparing tissue samples for sectioning. The method includes the steps of placing a tissue sample or specimen on a planar surface inside a cup-shaped receptacle, then pouring or applying O.C.T. into the receptacle in an amount sufficient to cover the specimen. Next, a chuck member, having a planar surface sized to be received within the cup-shaped receptacle, is inserted into the receptacle. The O.C.T. forms a barrier between the chuck planar surface and the specimen so that the specimen does not adhere to the chuck. The assembly of the receptacle and chuck with the O.C.T. and specimen therebetween is exposed to a temperature low enough to quickly freeze the specimen and the O.C.T., creating a solidified block of O.C.T. with the specimen embedded therein. The solidified block is then sliced for examination.

According to another aspect of the present invention, a method is disclosed for preparing a tissue specimen for sectioning, including the steps of: providing a cup-shaped receptacle having a first generally planar surface; providing a chuck member having a second generally planar surface sized to be received within said receptacle; placing a tissue sample on said receptacle planar surface; pouring a substance in liquid form into said receptacle; inserting said second planar surface into said receptacle; decreasing the temperature of said substance at least to its freezing point such that said that substance forms a solidified block with the specimen frozen therein.

According to another aspect of the invention, a method is disclosed for conveniently forming a solidified block of O.C.T. with tissue embedded therein on a chuck. The chuck, loaded with solidified O.C.T. and tissue, is then easily carried to a microtome for slicing while preserving the orientation of the flattened tissue surface.

According to another aspect of the invention, a device is disclosed for facilitating the alignment of a chuck member in a cup-shaped receptacle which thereby assists in orienting the chuck to the tissue specimen. In disclosed embodiments, the alignment device is configured with a handle that is spaced from the assembly of the chuck member and the receptacle. The handle allows the user to dip the entire assembly of the chuck member and the receptacle into liquid nitrogen for simultaneously freezing the specimen and encasing it in a solidified block of O.C.T.

According to another aspect of the invention, an assembly having a based for receiving a receptacle and a cap for orienting the chuck within the receptacle and for holding the chuck in proper orientation during dipping of the cup and chuck into a coolant, with the assembly having a handle portion spaced from the cup, such that a user can dip the receptacle and chuck in coolant while maintaining the proper orientation of the chuck in the receptacle.

According to another aspect of the invention, a kit is disclosed including a chuck and a mating receptacle for conveniently embedding a tissue sample in O.C.T. for frozen tissue sectioning.

BRIEF DESCRIPTION OF THE DRAWINGS

An exemplary version of a device and method for preparing tissue sections is shown in the figures wherein like reference numerals refer to equivalent structure throughout, and wherein.

DETAILED DESCRIPTION OF PREFERRED EMBODIMENT(S)

Figure 1:
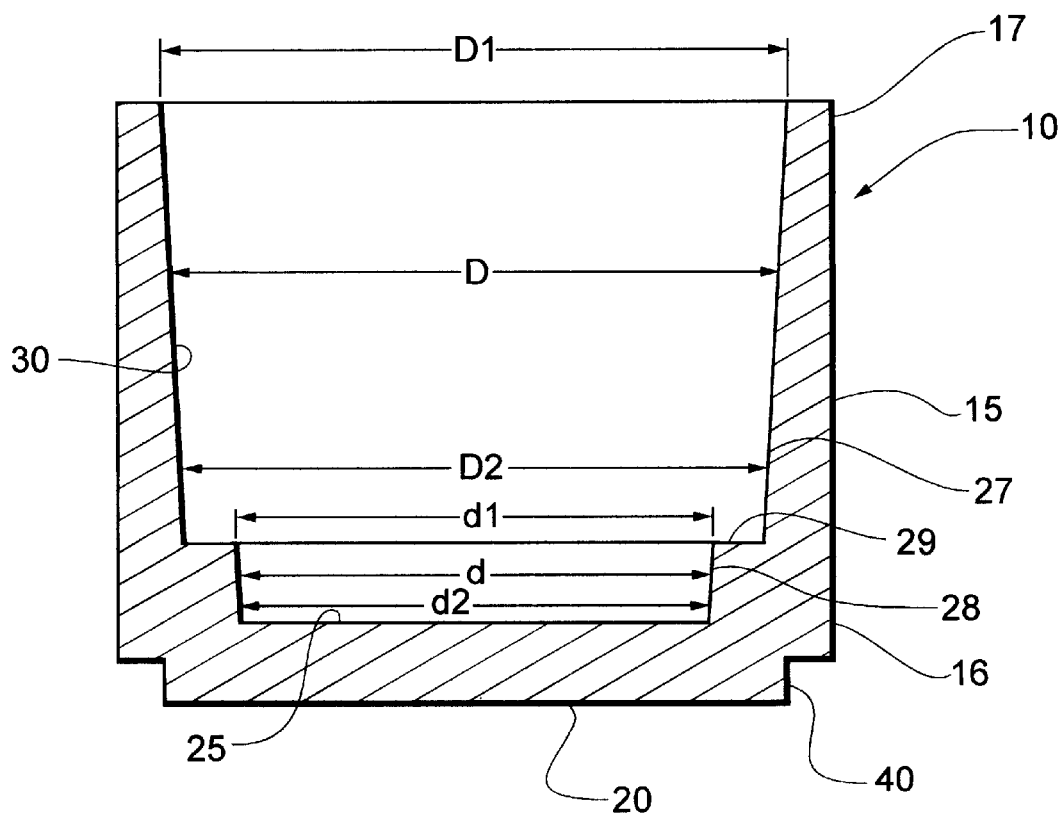
FIG. 1 is an enlarged cross-sectional view of a preferred embodiment of a cup-shaped receptacle according to the present invention.
Figure 2:
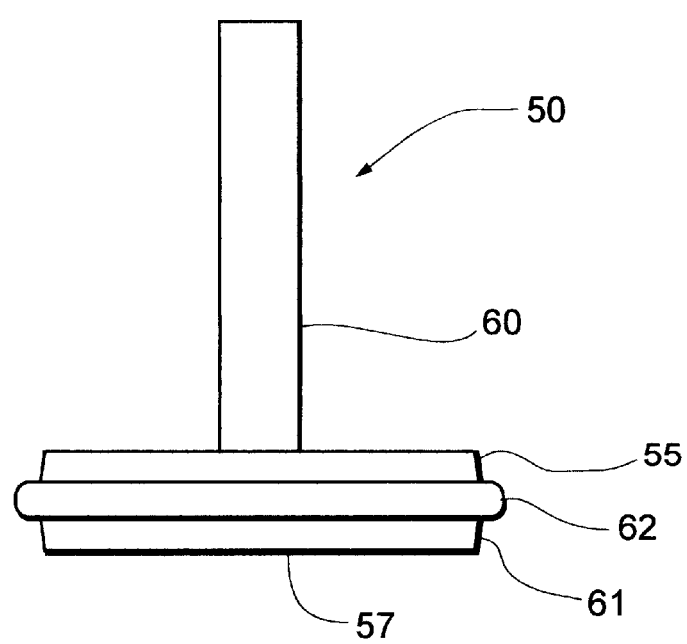
FIG. 2 is an enlarged side elevational view of a chuck member for use in conjunction with the receptacle of FIG. 1.

FIGS. 1 and 2 illustrate mating components for use in preparing a tissue sample to be sectioned for microscopic examination, such as during or in conjunction with frozen sectioning techniques for excising neoplasm.

A preferred embodiment of a cup-shaped receptacle 10 is illustrated in FIG. 1. The receptacle includes a generally cylindrical wall 15 that is capped at one end 16 with a closure member 20 having a generally planar internal surface 25. The end 17 of the cylindrical wall opposite the capped end 16 is open. In a preferred embodiment, the receptacle has a first portion or upper well 27, adjacent the open end 17, having a first internal diameter D, and a second portion or lower well 28, adjacent the capped end 16, having a second internal diameter d. Preferably D is greater than d. More specifically, a preferred angle of inclination of the internal surface of cylindrical wall 15 is between about 1 and 10 degrees, and most preferably between about 2 and 3 degrees. A ledge 29 is defined between portions 27 and 28. More specifically, ledge 29 extends generally radially between the internal surface of portion 27 and the internal surface of portion 28.

In a preferred embodiment of receptacle 10, the internal surface 30 of the cylindrical wall 15 slopes inward in the axial direction from open end 17 to capped end 16. In other words, the internal diameter D of portion 27 varies from D1 near the open end 17 to D2 near the second portion 28, and D1 is greater than D2. Further, in a preferred embodiment, the internal diameter d of second portion or well 28 varies from d1 adjacent portion 27 to d2 at the capped end 16, and d1 is greater than d2.

An annular recess 40 circumscribes the external surface of the capped end. This recess 40 facilitates the stacking of one receptacle 10 on top of another for storage, as will be described below.

FIG. 2 illustrates a chuck member 50 for use in conjunction with the cup-shaped receptacle illustrated in FIG. 1. A chuck member or chuck includes a head portion 55 having a generally planar surface 57. The head portion 55 is fixed to a generally elongated stem member 60. The head portion 55 of a preferred chuck member 50 terminates in a lowermost section 61 which bears planar surface 57. Adjacent section 61 is a center section 62. In a preferred embodiment, where head portion 55 is generally circular, section 62 has a greater diameter than section 61. In a most preferred embodiment, section 62 includes an circumferential gasket ring 65 that circumscribes the head portion 55. Preferably the gasket ring 65 is made of a resilient material. In alternate embodiments in which head portion 55 has a geometry that is not circular, section 62 exceeds section 61 in at least one dimension. Preferably, planar surface 57 is corrugated. Commercially available chuck members come in a variety of sizes and head shapes including but not limited to circular and rectangular. To accommodate chucks of various sizes and shapes, receptacles 10 can similarly be of various sizes and shapes. The exemplary receptacle illustrated in the drawings is shaped to receive a chuck having a circular head.

A preferred receptacle 10, FIG. 1, is sized and shaped to receive the chuck member 50 therein. More specifically, the internal diameter D of portion 27 is large enough to receive the head portion 55 of chuck member 50. Preferably, the internal diameter d of second portion 28 is smaller than the diameter of head portion 55 of chuck member 50, and therefore chuck member 50 can only be inserted into receptacle 10 until the head portion 55 of chuck 50 abuts ledge 29 in the receptacle 10. More specifically, in a preferred embodiment, diameter d1 is larger than the diameter of lower section 61 of head portion 55, but diameter d1 is smaller than the diameter of section 62 of the head portion 55. With such a configuration, the planar surface 57 protrudes into the lower well 28 of receptacle 10 when the chuck member 50 is in place in the receptacle 10 during use as described below.

Figure 3:
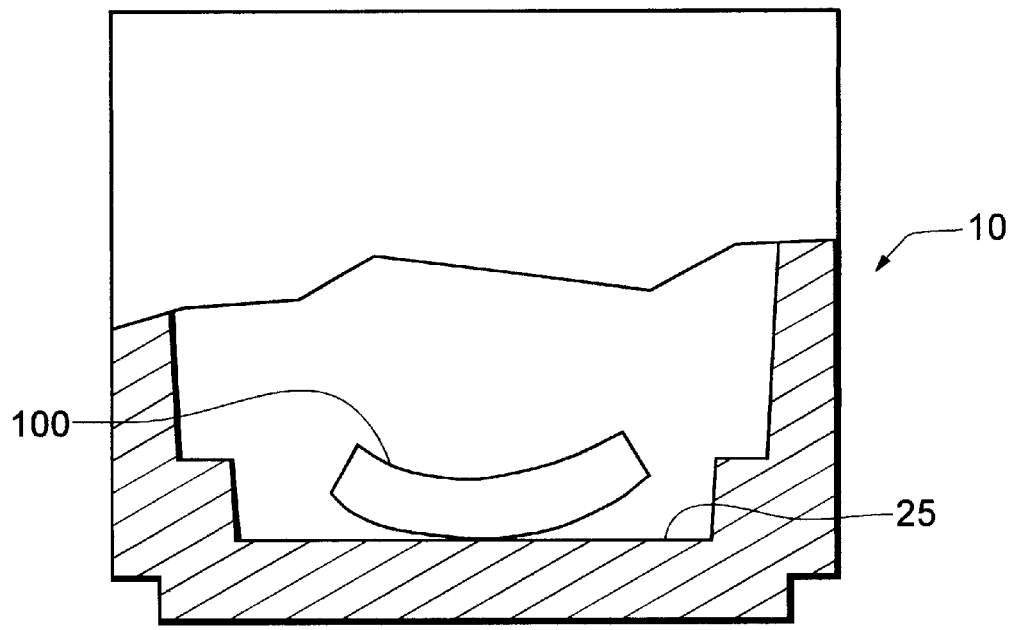
FIG. 3 is an enlarged side elevational view of the receptacle of FIG. 1, with portions shown in cross-section, with a tissue sample therein.
Figure 4:
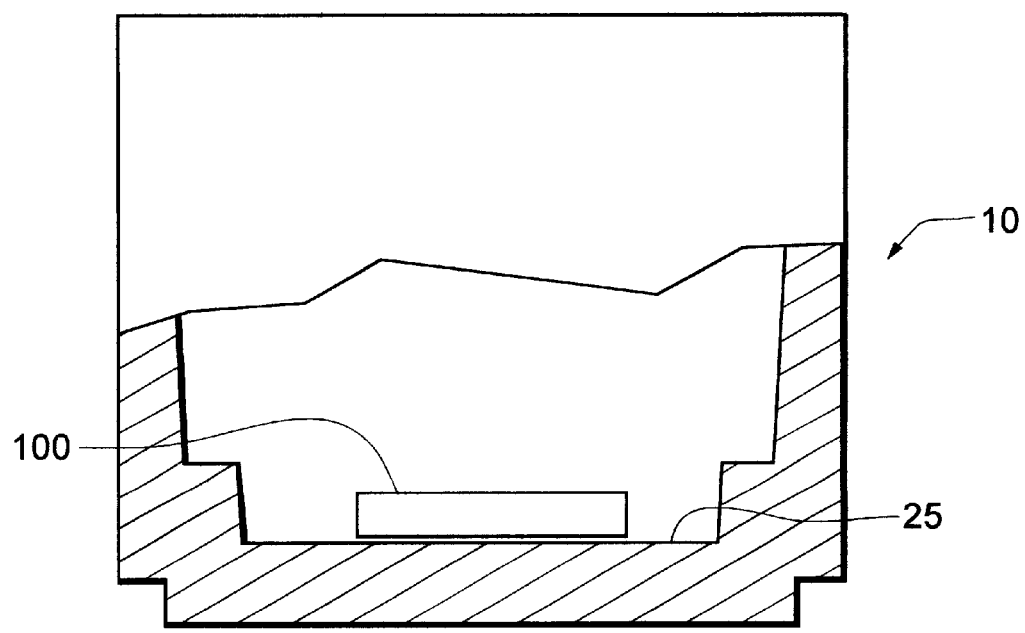
FIG. 4 is an enlarged side elevational view of the receptacle of FIG. 1, with portions shown in cross-section, with a tissue sample therein.

FIGS. 3–12 illustrate the method of preparing tissue samples for sectioning using the receptacle 10 and chuck member 50 of FIGS. 1 and 2. As illustrated in FIG. 3, a tissue sample 100 is placed inside the receptacle 10 on planar surface 25. Typically, a tissue sample will tend to curl somewhat at its edges as illustrated in FIG. 3. However, the sample is flattened against the planar surface by gravity and/or by adhesion to the planar surface 25 and/or by pre-cooling the receptacle 10 such that the tissue sample 100 freezes to the planar surface 25. FIG. 4 illustrates a flattened tissue sample 100 in the receptacle 10.

Flattening of the specimen is of particular importance in tumor margin analysis, but can also be advantageous, though not always necessary, for general diagnostic frozen sectioning. For tumor margin analysis, flattening is important to yield slices having a maximum surface possible of the total margin. Failing to flatten reduces the efficacy of the technique and thereby reduces the likelihood of total extirpation, increases the risk of tumor recurrence and increases the time and effort to fully examine the tissue margin.

Figure 5:
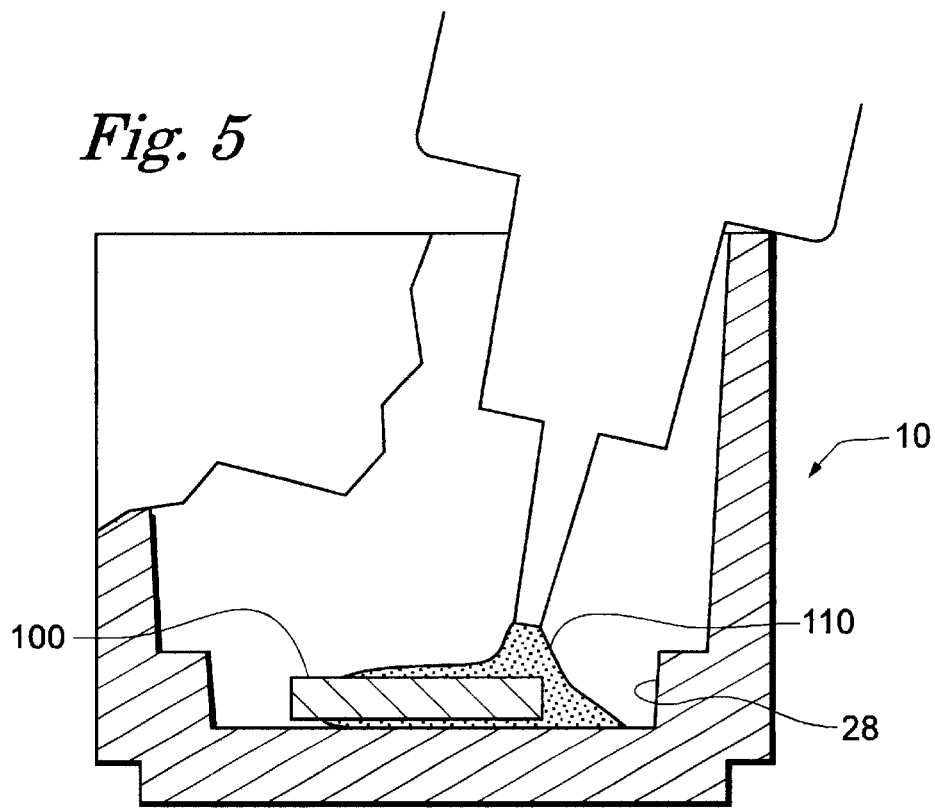
FIG. 5 is an enlarged side elevational view of the receptacle of FIG. 1, with portions shown in cross-section, with a tissue sample therein and illustrating the filling of the receptacle with an O.C.T. substance.
Figure 6:
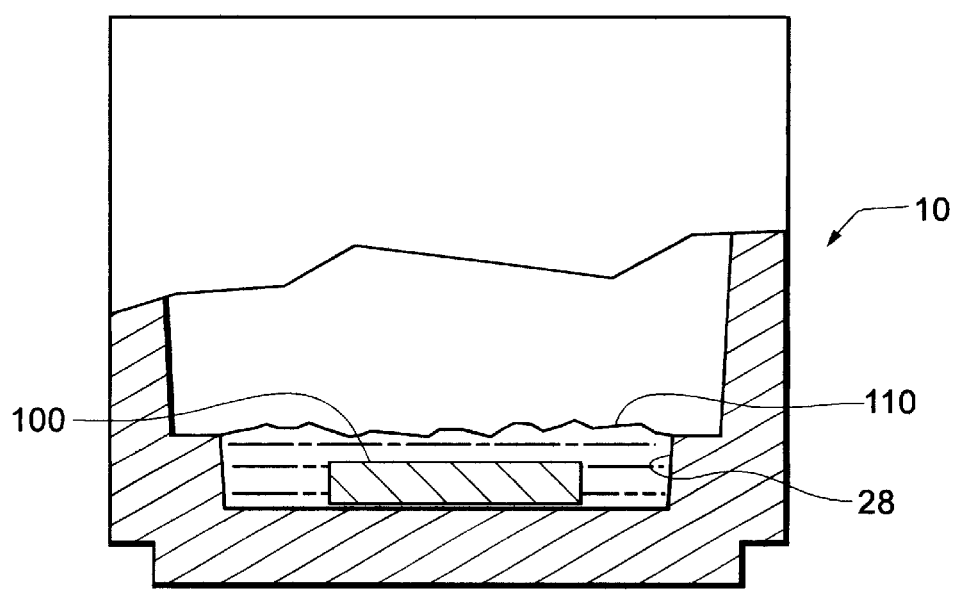
FIG. 6 is an enlarged side elevational view of the receptacle of FIG. 1, with portions shown in cross-section, with a tissue sample therein and illustrating the disposition of the tissue in a pool of O.C.T. substance.

As illustrated in FIG. 5, a substance 110 is poured into the receptacle. Substance 110 is an embedding compound typically referred to as O.C.T. An example of O.C.T. is sold commercially under the name Tissue-Tech™ and is manufactured by Sakura Finetech, Inc. of Terrence, Calif. O.C.T. is preferably liquid or semi-liquid at typical room temperature. As illustrated in FIG. 6, the user fills the lower well 28 of the receptacle 10 with substance 10. Tissue sample 100 is covered by the substance 100. The ledge 29 serves as a visual indication of the minimum amount of O.C.T. that should be supplied. The device and method of the present invention will function effectively if an overage of O.C.T. is provided.

Figure 7:
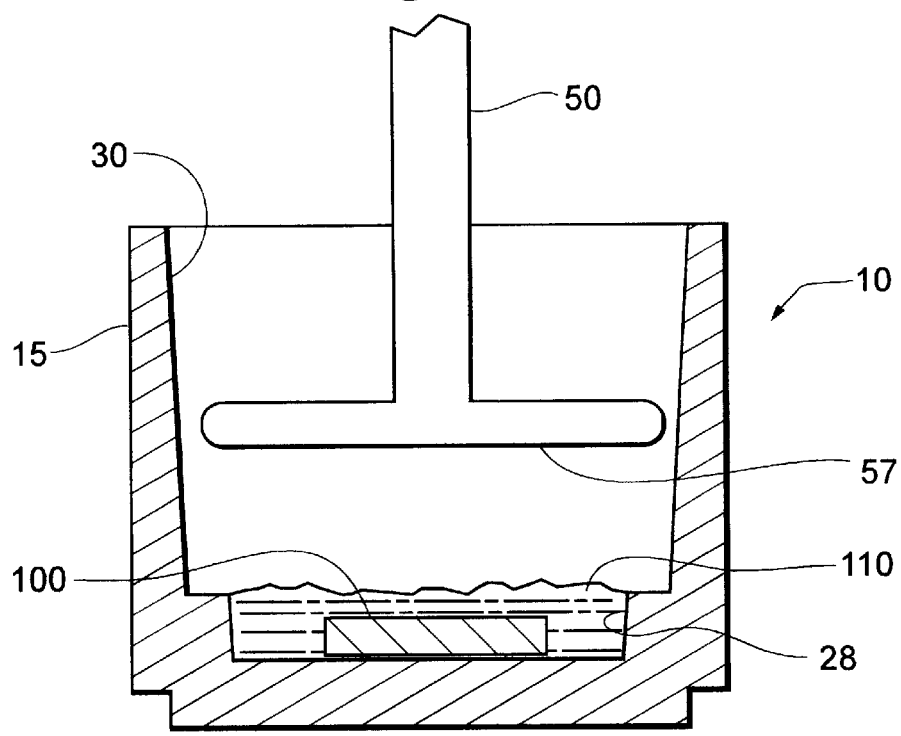
FIG. 7 is an enlarged side elevational view of the receptacle of FIG. 1, with portions shown in cross-section, with a tissue sample therein and illustrating the introduction of the chuck of FIG. 2 into the receptacle.
Figure 8:
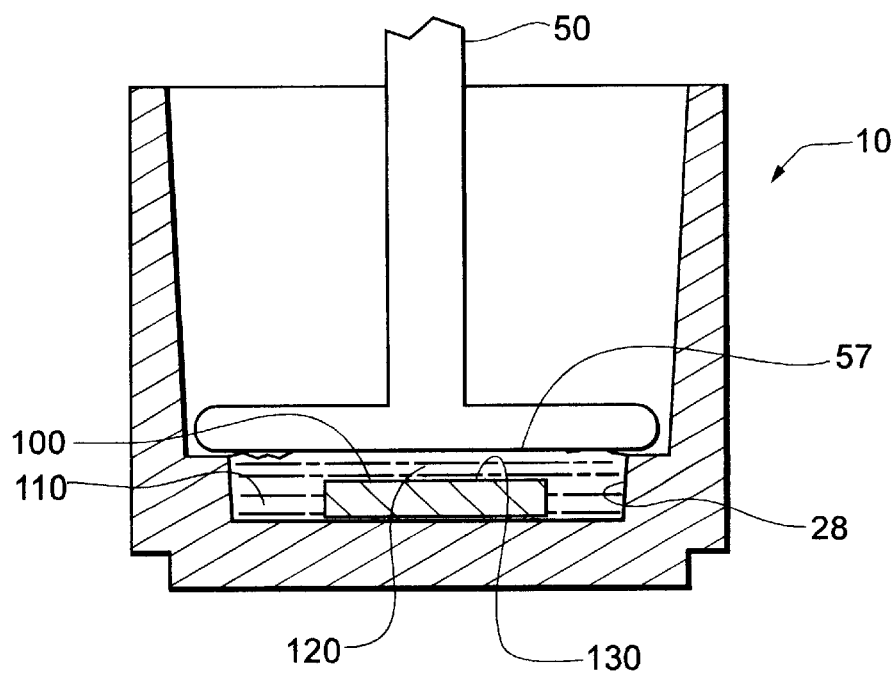
FIG. 8 is an enlarged side elevational view of the receptacle of FIG. 1, with portions shown in cross-section, with a tissue sample therein and illustrating the chuck member of FIG. 2 in a fully inserted position in the receptacle.

As illustrated in FIG. 7, a chuck member 50 is introduced into receptacle 10. The internal surfaces 30 of cylindrical wall 15 guide the chuck member into proper position, i.e. centered over the lower well 28 in which the specimen lies. As illustrated in FIG. 8, the chuck member 50 is pressed downward against the ledge 29. In a preferred embodiment, section 61 of chuck member 50 protrudes into the O.C.T. but does not protrude far enough into lower well 28 to contact the tissue 100. Because the chuck member 50 is illustrated schematically in FIGS. 7 and 8, this is not depicted. In an alternate embodiment, no portion of the chuck member 50 protrudes into lower well 28.

A portion 120 of the O.C.T. acts as a barrier or protective layer between the chuck and the tissue sample. In other words, because the depth of the well 28 is greater than the height of the tissue sample, and because the diameter d1 of the lower well is less than the diameter of the chuck head 55 (or the protruding section 61 of the chuck head 55), the gap or space 130 is maintained between the upper surface of the tissue and the planar surface 57 of the chuck 50. In this manner the tissue sample is protected from damage or deformation that could be caused by if the chuck member 50 were pressed directly against the tissue specimen.

Next, the assembly of the receptacle, tissue sample, O.C.T. and chuck member are subjected to a temperature sufficiently low to freeze the tissue and solidify the O.C.T., thereby creating a block 150 of solidified O.C.T. 112 with the frozen tissue sample 111 embedded therein. Freezing can be accomplished in a variety of ways. For example, the assembly can be allowed to cool relatively slowly in air at a temperature below freezing. Alternatively, the assembly can be sprayed with a coolant. A preferred method of cooling is by dipping the assembly in a bath of liquid nitrogen. This will be described in greater detail below in conjunction with a description of a holding assembly to facilitate dipping.

Figure 12:
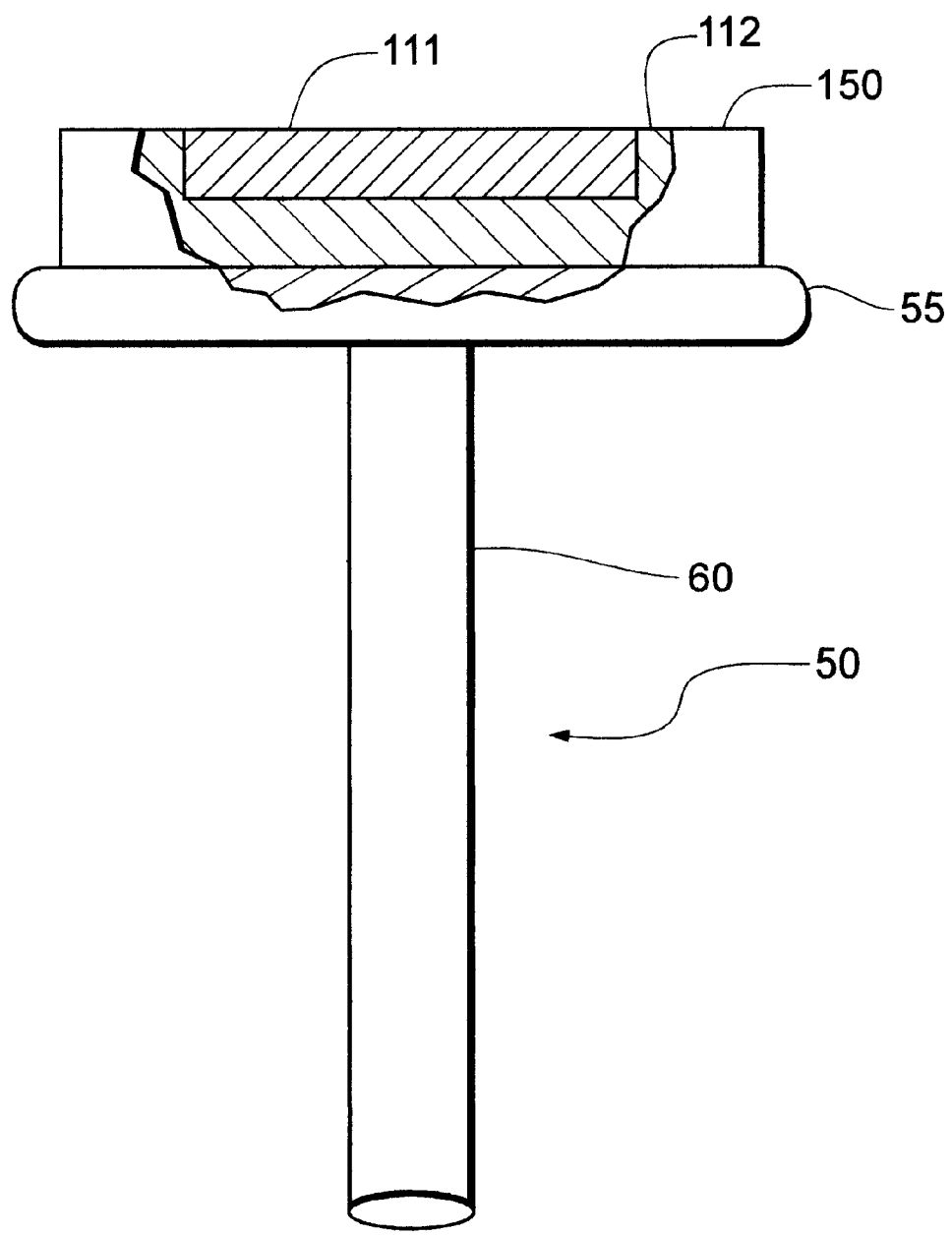
FIG. 12 is a side elevational view, with portions shown in cross-section, of a chuck member with a solidified block of O.C.T. with a tissue sample embedded therein.

As noted above, a preferred chuck member 50 has a corrugated surface. As a result, the solidified block has a tendency to stick to the chuck member 50 rather than to the receptacle, as illustrated in FIG. 12. Further, as noted above, the receptacle 10 has inclined internal walls which aid in removing the chuck 50, with block 150 attached thereto, from the receptacle 10 after freezing. More specifically, after freezing the block 150 may at least initially adhere to, or be expanded against, the wall of the receptacle 10 in the lower well 28. However, with manipulation that bond is broken relatively easily and the inclined walls of the receptacle provide clearance for the block 150 to be removed cleanly from the receptacle 10. The chuck member 50 can then be placed in a cryostat where histolgic sections are cut.

Figure 9:
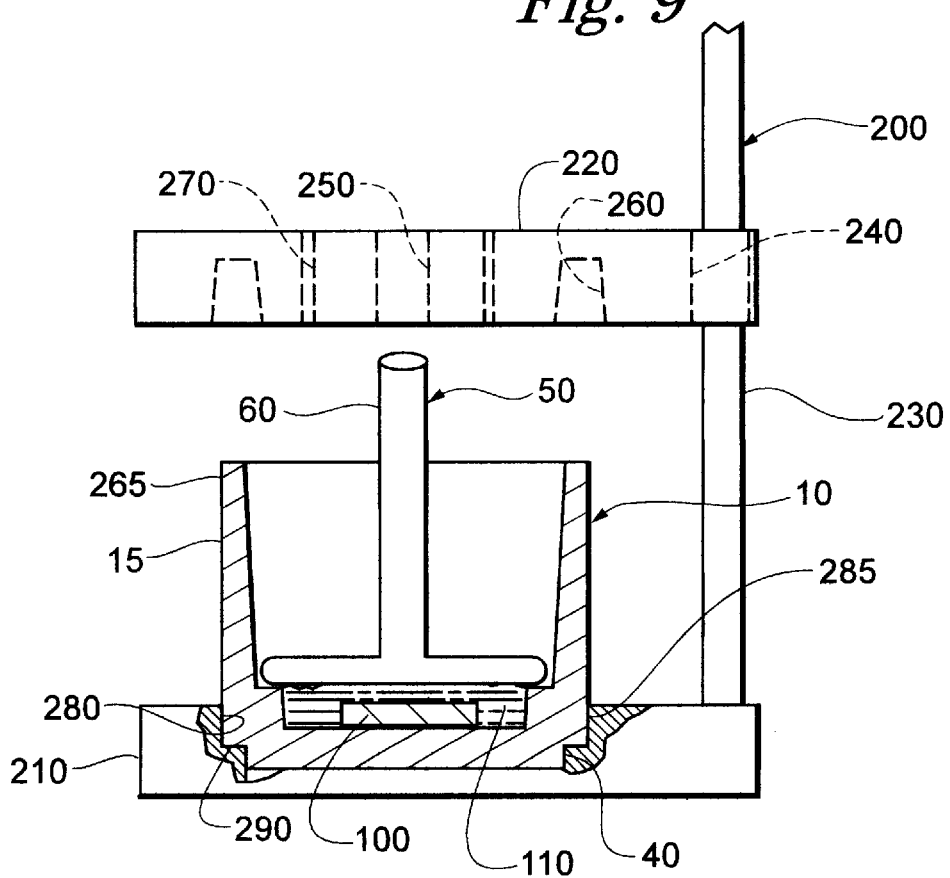
FIG. 9 is a fragmented side elevational view of a device for aligning the chuck member of FIG. 2 within the receptacle of FIG. 1.
Figure 10:
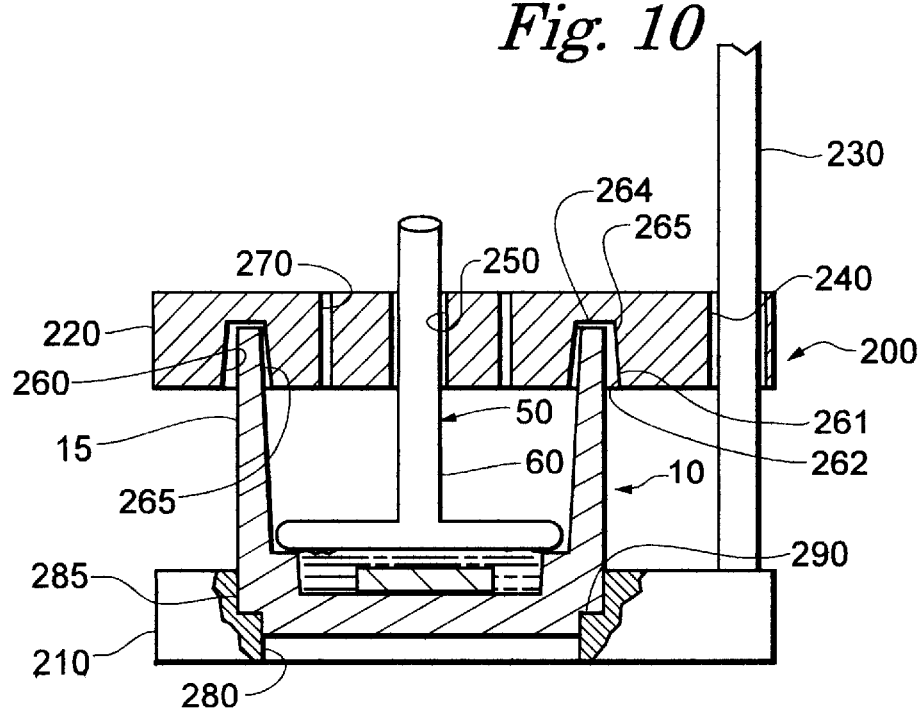
FIG. 10 is a fragmented side elevational view of the alignment device illustrated in FIG. 9.
Figure 11:
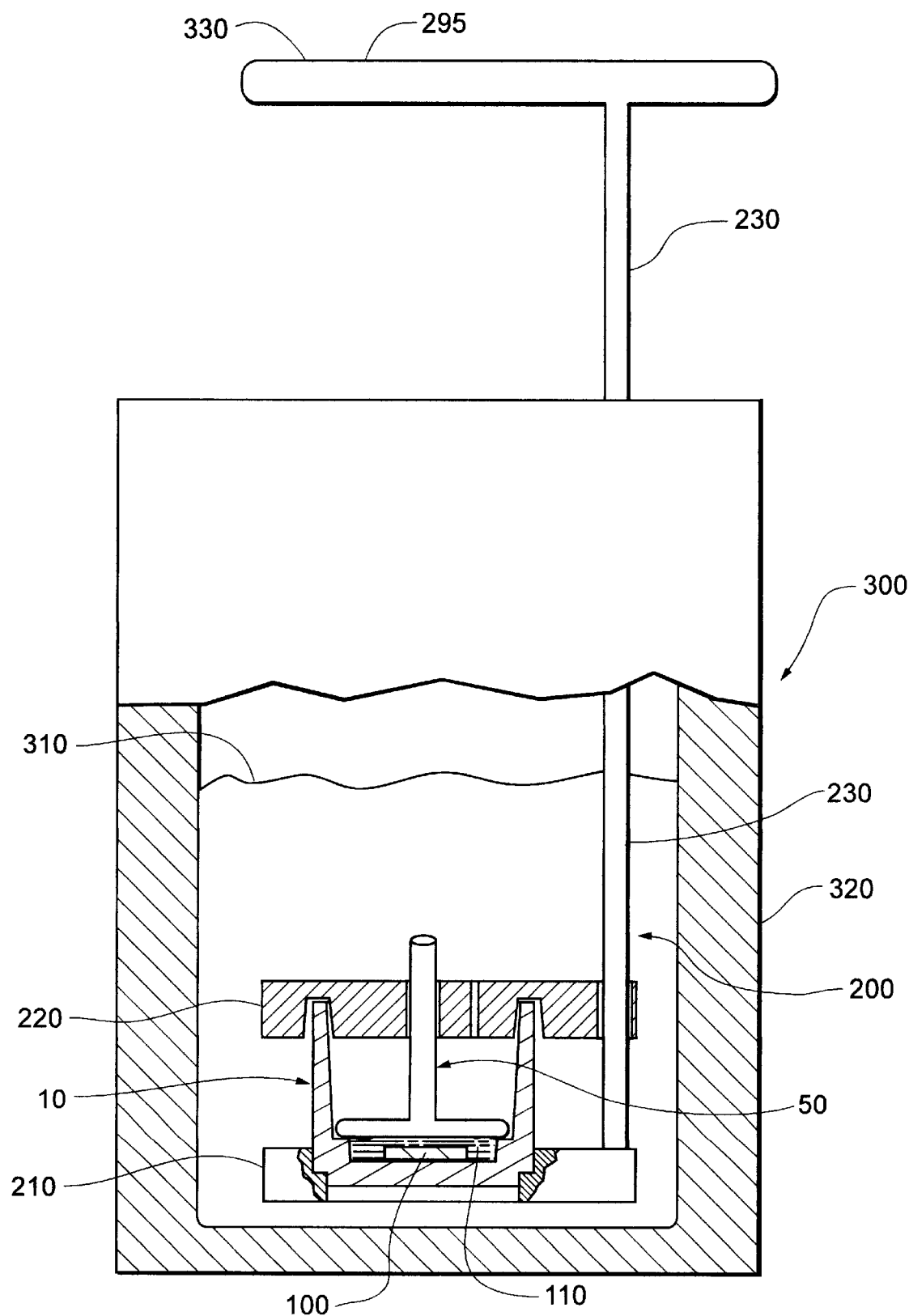
FIG. 11 is a side elevational view, with portions shown in cross-section, of the alignment device of FIG. 9 holding a receptacle and chuck member in position while the entire assembly is dipped in a pool of cooling liquid or gas.

FIGS. 9–11 illustrate a preferred embodiment of a dipping assembly 200 that holds the chuck member 50 in position in the receptacle 10 and allows a user to easily freeze the assembled receptacle 10, chuck member 50, tissue 100 and O.C.T. 100. The assembly 200 includes a base member 210 and a cap member 220. The base 210 and cap 220 are indirectly connected to one another for slidable movement of the cap 220 and base 210 with respect to one another, through a guide rod 230. Guide rod 230 is fragmented in FIGS. 9 and 10. More specifically, in the preferred embodiment illustrated, the base 210 is fixed to rod 230. Cap 220 defines a recess 240 therethrough for slidably receiving the rod 230. Preferably, the recess 240 is sized to allow cap 220 to slide on rod 230. Cap 220 further defines an aperture 250 therethrough for receiving the stem 60 of a chuck member 50. The underside 255 of the cap 220 defines a recess 260 for receiving a portion 265 of the wall 15 of the receptacle 10. The recess 260 preferably does not pass all the way through the thickness of the cap and is sized and shaped to mate with receptacle wall 15. In a preferred embodiment, the receptacle wall 15 is circular in cross-section, and therefore the recess 260 is annular. The radial width of the annular recess 260 is preferably slightly larger than the thickness of the wall 15. In a preferred cap 220, at least a portion of recess 260 is beveled or graduated such that it is wider or larger where it opens to receive receptacle 10 than it is at its closed portion. In the embodiment illustrated in FIG. 10, the recess 260 is beveled through a portion of the recess' depth. Portion 261, adjacent its open end 262 is beveled; portion 263, adjacent the closed end 264 is not beveled or is square in cross-section. This beveling provides ease in centering the cap 220 relative to the receptacle 10. Further, frozen condensation tends to form between close surfaces during freezing. Therefore it is advantageous for gaps between mating surfaces to be far enough apart that condensation is less likely to fill the gap therebetween and freeze the mating surfaces together during typical use. Aperture 250 is similarly beveled in a preferred embodiment.

A preferred cap 220 defines a plurality of holes 270 therethrough for enhanced heat transfer and reduced coolant consumption during freezing. More specifically, heat transfer is enhanced because the holes descrease the mass of material that must be cooled, and also because it facilitates convective heat transfer, i.e. direct heat transfer between the coolant or cooled environment and the interior of the receptacle 10.

Base 210 defines a recess 280 for receiving at least a portion 285 of receptacle 10. Preferably, recess 280 is contoured to mate with the external surface of receptacle 10. In the illustrated embodiment, receptacle 10 has an annular ring 40 around its bottom surface. Accordingly, recess 280 in base 210 is stepped or has a ledge 290 to mate with the contours of the annular ring 40.

In a preferred embodiment, the stem recess 250, the annular ring recess 260, and the rod aperture 240 are defined by beveled or inclined walls to facilitate removal or movement after freezing. Beveling these surfaces also reduces problems of frozen condensation during repeat uses.

In a preferred embodiment, the dipping assembly 200 incorporates a gripping portion 295, illustrated in FIG. 11, that is thermally insulated from the base 210. In a preferred embodiment, this gripping portion is insulated simply by its distance from the base, i.e. by the length of the guide rod 230 to which it is attached. The distance required to adequately insulate the gripping portion depends upon the material used for the dipping assembly 200 and upon the size and shape of parts used, i.e. the volume of material, in the dipping assembly. For an anodized aluminum dipping assembly, having a base and cap that are slightly larger in circumference than a cylindrical receptacle of the size illustrated in FIG. 13, and having a guide rod with a diameter of about one quarter inch, the gripping portion is preferably spaced between about 16 inches and 20 inches from the base. As will be apparent from the description below, this thermal insulation of the gripping portion 295 from the base is advantageous during use because a user can hold the gripping portion 295 while dipping the base, with the receptacle therein, into a coolant such as liquid nitrogen, without having to let go of the assembly while at the same time protecting the user's hands from the coolant.

In the embodiment illustrated in FIG. 11, the gripping portion 295 is a handle 330 that is fixed to the guide rod 230 and in generally tangential thereto.

In use, a user places the assembly of the receptacle 10, with tissue 100 and OCT 110 therein, and the chuck member 50, into the recess 280 in base 210. The user then slides cap 220 along rod 230 into position above the receptacle. A portion of the chuck stem 60 passes through aperture 250 and is thereby maintained in position with the planar surface 57 perpendicular to the plane of the tissue specimen in the receptacle 10. A portion 265 of wall 15 in receptacle 10 in received within the recess 260 in the cap 220, but does not pass entirely therethrough.

The device 200, with the cup, chuck, tissue and OCT resting between cap 220 and base 210, is then placed in an environment having a temperature sufficiently low to freeze the OCT and the tissue. As illustrated in FIG. 11. In a preferred method, the freezing environment is a liquid nitrogen bath 300. A pool of liquid nitrogen 310 is contained in a container 320, such as a thermos. The rod 230 of the holding assembly 200 is elongate and preferably terminates in a handle portion 330 for the user to hold to put the assembly into the bath 300 and to remove it after freezing, without exposing his/her skin to the bath 300. After freezing, the user lifts the assembly out of the bath 300 and lifts and swings the cap 220 away from the receptacle 10. The receptacle and chuck member are removed from the base 210. After briefly warming the receptacle and chuck member, the user removes the chuck member with the solidified block 150 adhered thereto and places the chuck in a cryostat and histologic sections are cut.

Figure 13:
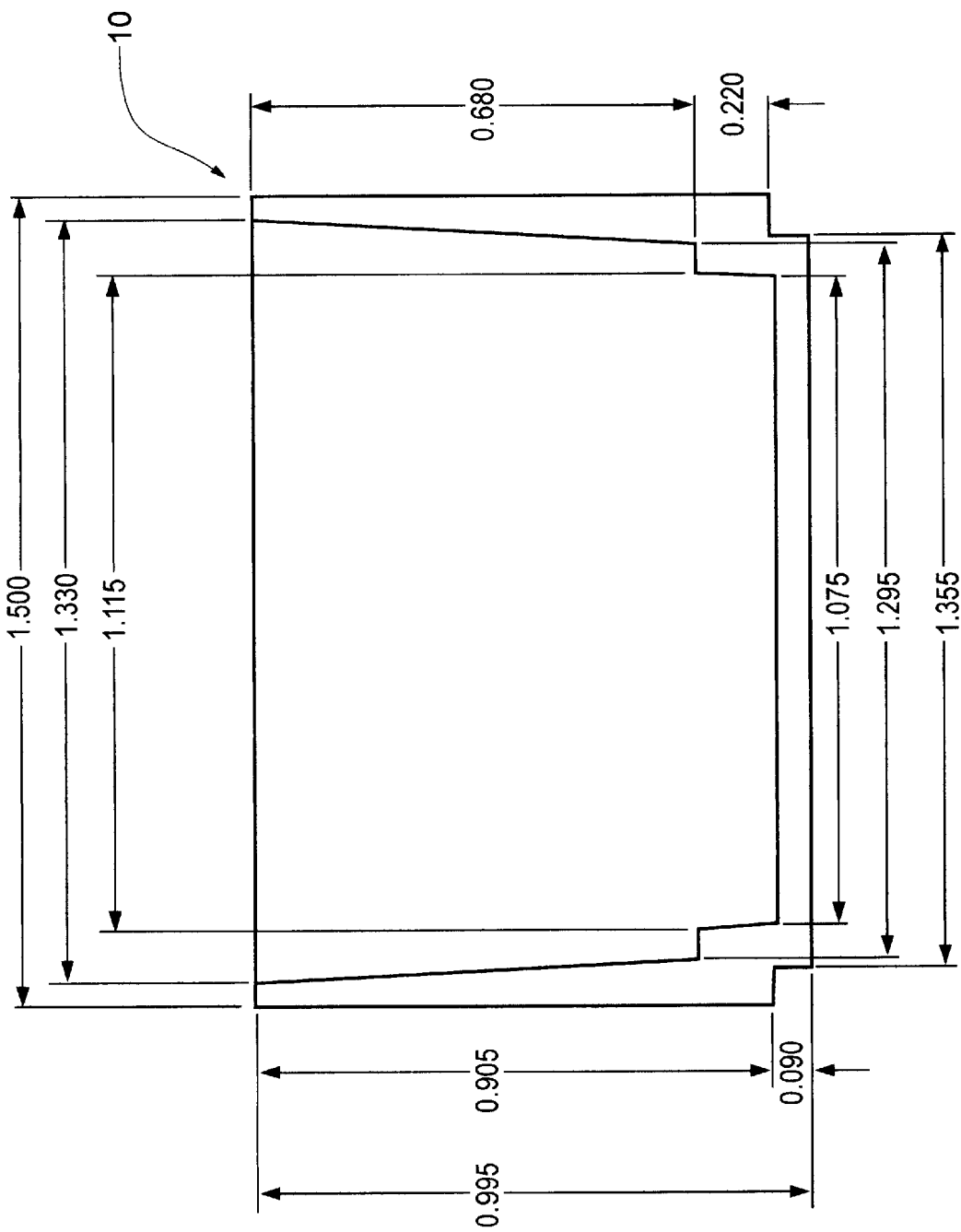
FIG. 13 schematically illustrates the dimensions of one embodiment of the receptacle of FIG. 1.

FIG. 13 illustrates the dimensions of a preferred embodiment of receptacle 10 for receiving most commercially available chuck members. It should be understood, however, that the invention is limited only by the scope of the appended claims, and that cups and chucks of any dimensions and geometric design can be used within the spirit of this invention. The most preferable size will be determined by the particular application for which the receptacle 10 is being used, and by the size of the available or appropriate chuck member 50. In the embodiment illustrated in FIG. 13, D varies or is inclined or beveled from 1.330 inches to 1.295 inches; d varies or is inclined or beveled from 1.115 inches to 1.075 inches. The depth of the lower well 28 is 0.220 inches; the depth of upper well 27 is 0.680 inches. The height of the entire receptacle 10 is 0.995 inches. The height of the annular recess 40 if 0.090. The outer diameter of the receptacle 10 is 1.50 inches, and the outer diameter of the receptacle at the annular recess 40 is 1.355 inches.

Figure 14:
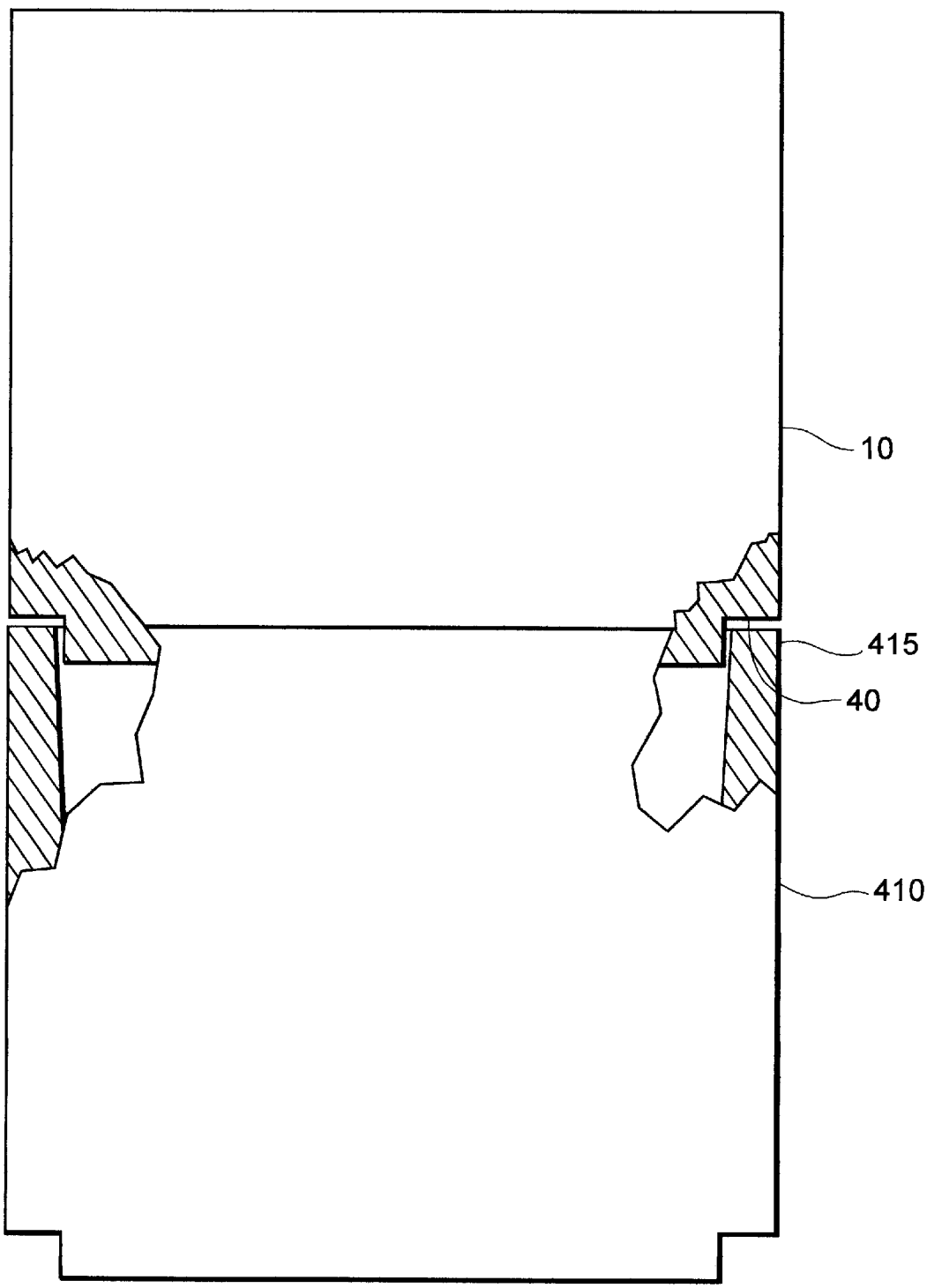
FIG. 14 is a side elevational view, with portions shown in cross-section, of two receptacles like that illustrated in FIG. 1 stacked on top of one another.

FIG. 14 illustrates how multiple cups having annular rings 40 can be stacked on top of one another for convenient shipping and storage. Ring 40 in one receptacle 10 receives the upper edge of wall 415 of an adjacent receptacle 410.

Figure 15:
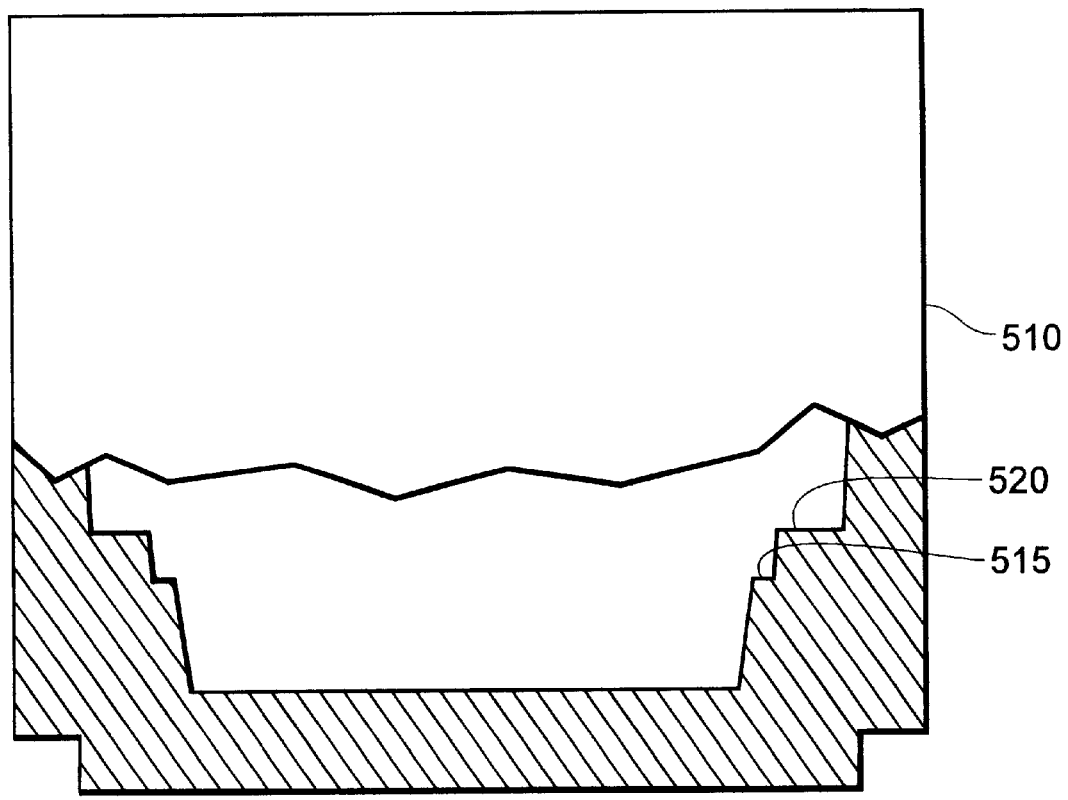
FIG. 15 is a side elevational view, with portions shown in cross-section of an alternate embodiment of a receptacle according to the present invention.

In is contemplated that a receptacle according to the present invention may have any number of ledges defined by its internal walls. This arrangement variety is advantageous for accommodating a variety of chuck sizes and geometries. FIG. 15 illustrates one such alternate embodiment of a receptacle 510. The internal surface of receptacle 510 defines two steps or ledges 515, 520. In addition, the arrangement provides wells of two different depths for increasing the versatility of the receptacle 510.

Figure 16:
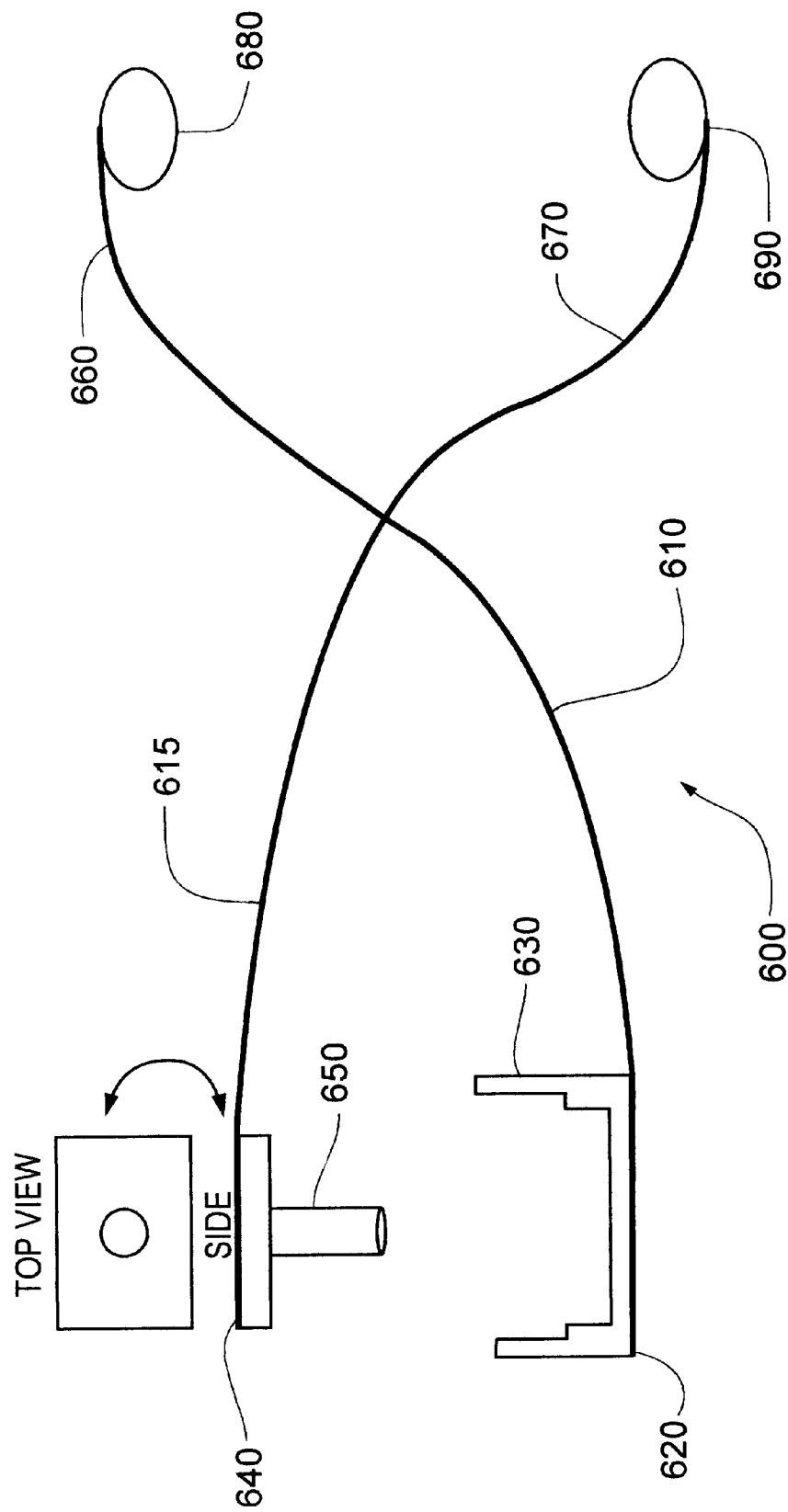
FIG. 16 is a side elevational view of an alternate embodiment of a device for aligning a receptacle and chuck member.

FIG. 16 illustrates an alternate embodiment of a holding assembly 600. The device 600 is configured like tongs, with first and second members 610, 615 pivotally connected to one another. Attached to one end 620 of member 610 is a receptacle cup 630. Alternatively, end 620 may be configured to receive a separate receptacle cup. Attached to one end 640 of member 615 is a chuck member 650. Alternatively, end 640 may be configured to receive or accommodate a separate chuck member. The opposite ends 660, 670 have handles 680, 690 for manipulating the position of the opposite ends 620 and 640 for moving the chuck 650 into and out of position within the cup 630. Preferably, members 610 and 615 are long enough to allow a user to hold the handles 680 and 690 and dip the opposite ends in a liquid nitrogen bath without exposing his/her skin to the bath.

Figure 17:
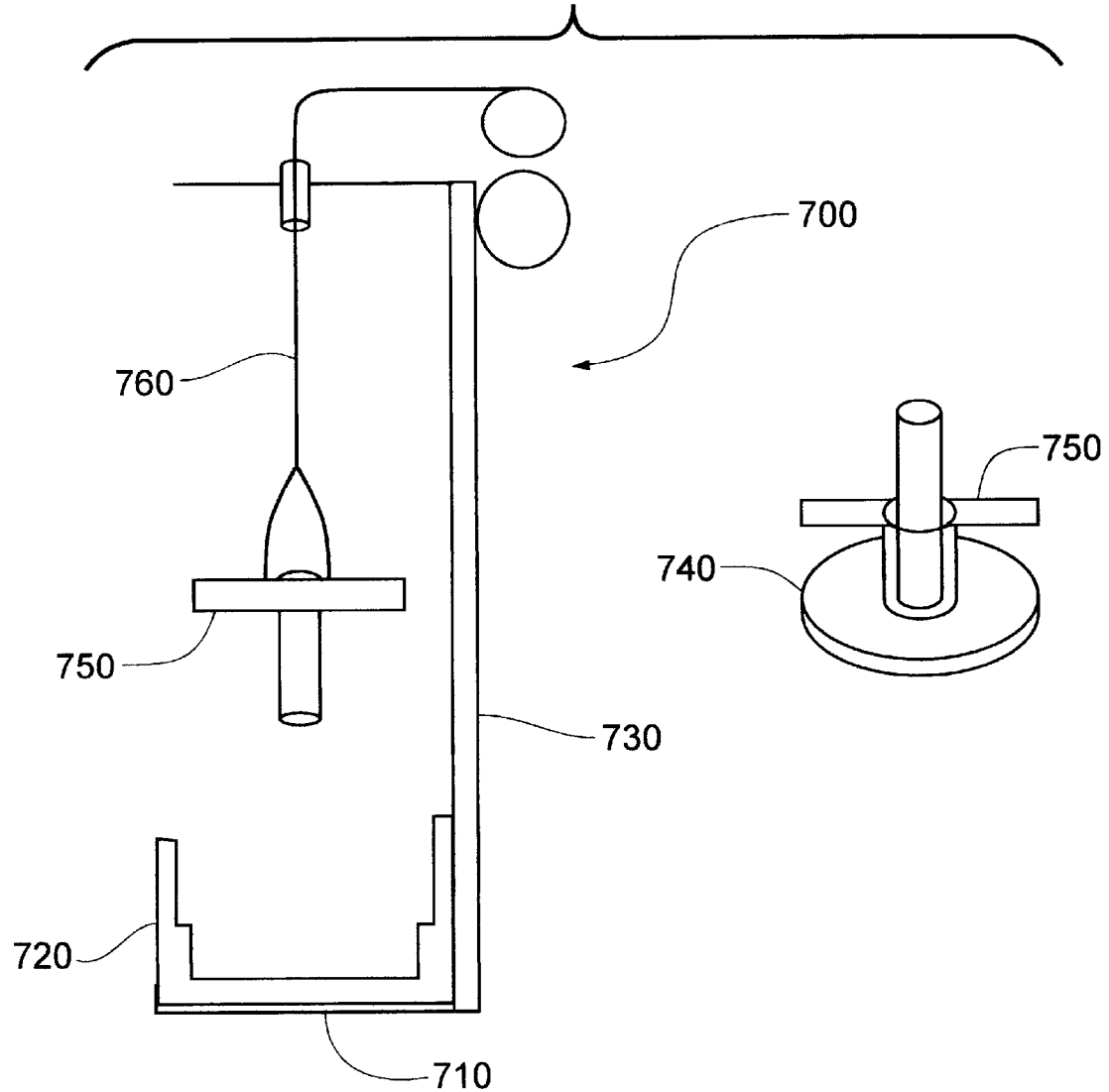
FIG. 17 is a side elevational view of an alternate embodiment of a device for aligning a receptacle and chuck member.

FIG. 17 illustrates another alternate embodiment of a holding assembly 700. This assembly 700 incorporates a base 710 for holding a receptacle 720. The base 710 is attached to one end of an elongate rod or stand 730. A chuck member 740 is removably attached to a chuck holding member 750 which in turn is connected by a flexible line 760 to the rod 730. Preferably, the flexible line 760 can be wound or unwound from a spool to raise or lower the chuck member out of or into the receptacle as desired.

Figure 18:
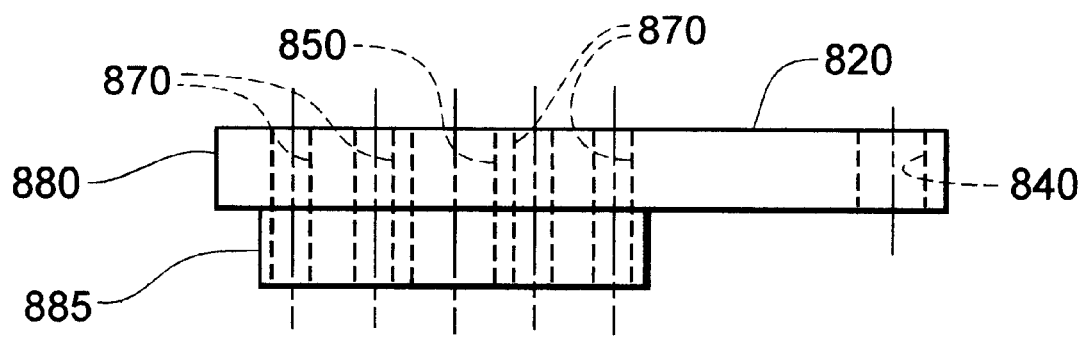
FIG. 18 is an enlarged side view of an alternate embodiment of a cap for use in conjunction with the assembly of FIG. 9.
Figure 19:
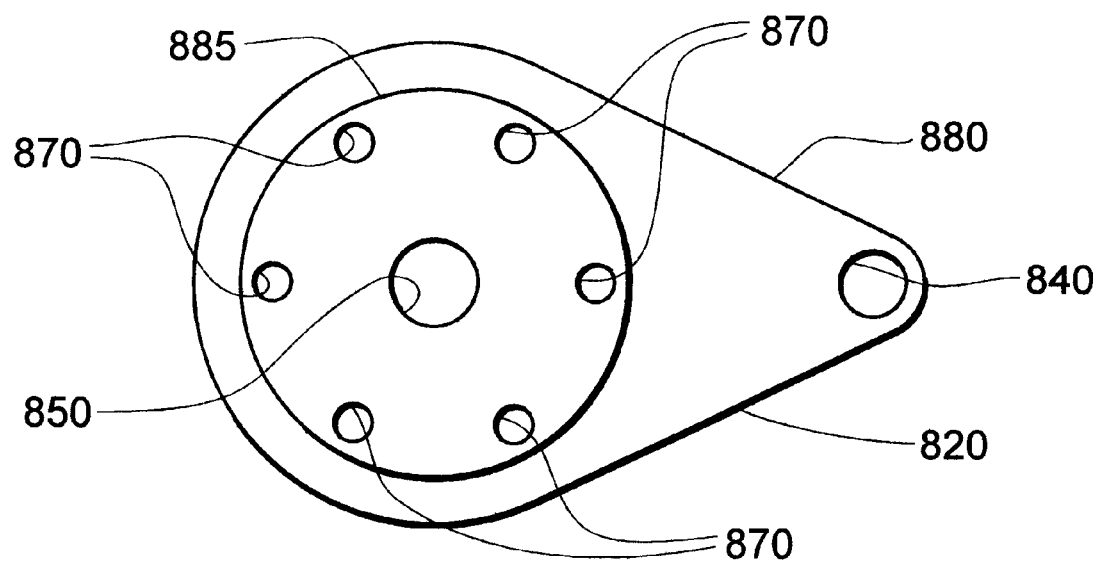
FIG. 19 is an enlarged bottom view of the cap embodiment of FIG. 18.

FIG. 18 illustrates an alternate embodiment of a cap 820 for a dipping assembly 200 such as that described above with reference to FIGS. 9–11. Like cap 220, cap 820 has a generally center aperture 850 for receiving the stem 60 of a chuck 50. Cap 820 further includes an aperture 840 for receiving a guide rod 230 of a dipping assembly 200. Apertures 870 are advantageous for enhancing heat transfer during cooling because they decrease the mass of the cap 820 and because they facilitate convective heat transfer between the cooling environment and the interior of the receptacle. The cap 820 illustrated in FIG. 18 has a guide-rod-engaging portion 880 and a receptacle-engaging portion 885 that protrudes therefrom. Portion 880 extends longitudinally generally between the guide rod of a dipping assembly and the portion of the cap that engages a receptacle. As illustrated in FIG. 19, the portion 880 has a tear drop circumferential shape, though other shapes are possible as described below.

Protruding portion 885 has a circumferential shape and size that fits within the receptacle being used. In the illustrated cap 820, portion 885 has a circular circumferential shape to be received within a receptacle having a generally cylindrical wall. As oriented in use, the protruding portion 885 protrudes generally downwardly from the portion 880.

As noted above, a preferred circumferential shape for portion 880 of cap 820 is tear-dropped. Preferred cap 220 similarly has a tear-drop circumferential shape. Other circumferential shapes for cap 220 and 820, such a rectangular, oval, square, circular or irregular, are also within the spirit of this invention. The tear-drop shape is advantageous because it has a relatively small amount of mass while accommodating a circular-shaped protruding portion 885 which in turn accommodates a cylindrical receptacle which in turn accommodates a common circular chuck. As discussed above, the chuck may be of any shape and a receptacle is shaped to accommodate the chuck being used, and therefore protruding portion 885 is shaped to fit within the receptacle, and portion 880 is sized and shaped to support protruding portion 885.

A preferred receptacle 10 is made of inert, rigid material. Preferably, the receptacle is re-usable and is cast of aluminum which is anodized for appearance and durability. The anodization can be in a variety of colors and the colors may be used randomly or can be coded to types of tissue samples or tests to be conducted on tissue samples. However, other materials can be used within the spirit of this invention. For example, the receptacle 10 can be molded of plastic. Alternate embodiments of receptacle 10 are coated on at least a portion of their interior surface with Teflon or other non-stick material to facilitate the removal of the chuck with the frozen O.C.T. and tissue sample adhered thereto.

Similarly, the preferred cap 220, base 210 and rod 230 is made of inert, rigid material. Preferably, the cap is re-usable and is cast of aluminum which is anodized for appearance and durability. However, other materials can be used within the spirit of this invention. For example, the cap 220 can be molded of plastic. Alternate embodiments of caps 220 are coated on at least a portion of their interior surface, i.e. the surface that is exposed to the interior of receptacle 10 in use, with Teflon or other non-stick material.

Although an illustrative version of the device is shown, it should be clear that many modifications to the device may be made without departing from the scope of the invention.

What is claimed is:

1. A device for entombing a tissue specimen, comprising:
    a) a cup-shaped receptacle;
    b) a chuck member having a planar surface and a stem extending therefrom;
    c) a base having a recess therein for receiving a cup-shaped receptacle;
    d) a chuck-receiving member having a recess therein for receiving said stem on said chuck member;
    e) a rod member fixed to said base with said chuck-receiving member slidably affixed thereto.

2. A device for entombing a tissue specimen according to claim 1, wherein:
    a) said cup-shaped receptacle has a first generally planar surface and has a lower well and an upper well, said lower well having a diameter smaller than said upper well, with a radially-extending ledge defined between said lower and upper wells;
    b) a chuck member has a second generally planar surface sized to be received within said receptacle and sized to pass through said upper well and sized to abut said ledge, such that said planar surface caps said lower well.

3. A device for entombing tissue specimens according to claim 2, wherein said lower well converges along its length in the direction toward said capped end, and wherein said upper well converges along its length in the direction toward said capped end, and wherein said inner diameter of said lower well is smaller than the smallest inner diameter in said upper well.

4. A device for entombing tissue specimens, according to claim 3, wherein said inner diameter of said upper well converges from 1.350 inches to 1.295 inches, and said diameter of said lower well converges from 1.115 inches to 1.075 inches and wherein said lower well is 0.220 inches in length.

5. A device for entombing tissue specimens according to claim wherein the receptacle's outer bottom surface defines an annular notch for receiving a portion of a second receptacle for convenient stacking of one receptacle on top of another.

6. A device for entombing tissue specimens according to claim 2, wherein said ledge is 0.023 inches wide.

7. A device for entombing tissue specimens in solidified substance, comprising:
    a) a cup-shaped receptacle having a first generally planar surface having a lower well and an upper well, said lower well having a diameter smaller than said upper well, with a radially-extending ledge defined between said lower and upper wells;

b) a chuck member having a second generally planar surface sized to be received within said receptacle and sized to pass through said upper well and sized to abut said ledge, such that said planar surface caps said lower well, with said chuck member planar surface having corrugations extending into said lower well when said chuck is positioned within said receptacle.

8. A dipping assembly for freezing a tissue specimen comprising first and second members each having first and second ends, said members pivotally connected to one another at a point between said ends, with one end of one said member being adapted to receive a chuck member and one end of the other said member being adapted to receive a cup-shaped receptacle, said first and second member being pivotally connected to one another at a point between said ends, such that upon spreading said second ends away from one another, said chuck-receiving member moves away from said receptacle-receiving member.

9. A device for entombing a tissue specimen according to claim 1, wherein said receptacle has three portions each having a different diameter with two radially-extending ledges, each ledge defined between two portions of differing diameter.

* * * * *